(12) United States Patent
Ruperez et al.

(10) Patent No.: US 9,200,997 B2
(45) Date of Patent: Dec. 1, 2015

(54) PHOTONIC SENSING METHOD AND DEVICE

(75) Inventors: Jaime Garcia Ruperez, Valencia (ES); Javier Marti Sendra, Valencia (ES); Alejandro Jose Martinez Abietar, Valencia (ES)

(73) Assignee: UNIVERSIDAD POLITECNICA DE VALENCIA CTT, CENTRO DE TRANSFERENCIA DE TECNOLOGIA (ES)

( * ) Notice: Subject to any disclaimer, the term of this patent is extended or adjusted under 35 U.S.C. 154(b) by 966 days.

(21) Appl. No.: 13/388,086

(22) PCT Filed: Jul. 21, 2010

(86) PCT No.: PCT/ES2010/070502
§ 371 (c)(1),
(2), (4) Date: Mar. 23, 2012

(87) PCT Pub. No.: WO2011/012753
PCT Pub. Date: Feb. 3, 2011

(65) Prior Publication Data
US 2012/0170041 A1 Jul. 5, 2012

(30) Foreign Application Priority Data
Jul. 31, 2009 (ES) .................................. 200901748

(51) Int. Cl.
*G01N 21/00* (2006.01)
*G01N 21/552* (2014.01)
(Continued)

(52) U.S. Cl.
CPC .............. *G01N 21/00* (2013.01); *G01N 21/552* (2013.01); *G02B 6/1225* (2013.01); *B82Y 20/00* (2013.01);
(Continued)

(58) Field of Classification Search
CPC ... G02B 6/305; G01N 21/253; G01N 21/7743
USPC ................................. 356/445, 459, 432, 317
See application file for complete search history.

(56) References Cited

U.S. PATENT DOCUMENTS

2006/0193552 A1  8/2006  Sugita
2008/0019648 A1*  1/2008  Atwater et al. ............... 385/122
2008/0278722 A1*  11/2008  Cunningham et al. ........ 356/317

FOREIGN PATENT DOCUMENTS

EP          1 942 341       7/2008
JP          2007-271609    10/2007
(Continued)

OTHER PUBLICATIONS

"Silicon-on-Insulator microring resonator for sensitive and label-free biosensing"—Opt. Express, vol. 15, 7610-7615 (2007)—K. De Vos et al.
(Continued)

*Primary Examiner* — Gregory J Toatley
*Assistant Examiner* — Iyabo S Alli
(74) *Attorney, Agent, or Firm* — Gerald E. Hespos; Michael J. Porco; Matthew T. Hespos

(57) ABSTRACT

This invention describes a photonic sensing method and device based on the periodic dielectric structures of photonic forbidden band, in which the sensing process is carried out through the measurement of variation in signal amplitude as it exits the device. The variation in amplitude is due to a variation in the refraction index of the structure, as a consequence of the presence of the substances that are the object of the sensing. Among the advantages provided by the invention, it is worth mentioning its simplicity in the sensing process; its high level of integration, allowing for a design of reduced proportions; and its adaptability to dielectric structures of one, two or three dimensions.

18 Claims, 5 Drawing Sheets

(51) Int. Cl.
*G02B 6/122* (2006.01)
*G02B 6/12* (2006.01)
*G01N 21/77* (2006.01)
*B82Y 20/00* (2011.01)
*G02B 6/124* (2006.01)

(52) U.S. Cl.
CPC .............. *G01N 21/774* (2013.01); *G02B 6/124* (2013.01); *G02B 2006/1213* (2013.01); *G02B 2006/12138* (2013.01)

(56) References Cited

FOREIGN PATENT DOCUMENTS

| | | |
|---|---|---|
| JP | 2008-014732 | 1/2008 |
| WO | 2008/151611 | 12/2008 |

OTHER PUBLICATIONS

"Polymer Microring Resonators for Biochemical Sensing Applications"—IEEE J. Sel. Top. Quantum Electron, vol. 12, 134-142 (2006)—Chung-Yen Chao et al.

"Photonic-crystal waveguide biosensor"—Opt. Express, vol. 15, 3169-3176 (2007)—Nina Skivesen et al.

"Refractive-index measurements using an integrated Mach-Zehnder interferometer"—Sens. Actuators A Phys. 60, 108-112 (1997)—Th. Schubert et al.

"Integrated-optical directional coupler biosensor"—Opt. Letters, vol. 21, 618-620 (1996)—B.J. Luff et al.

"Slot-waveguide biochemical sensor"—Opt. Letters, vol. 22, 3080-3082 (2007)—Carlos A. Barrios et al.

\* cited by examiner

PHOTONIC SENSING METHOD AND DEVICE

BACKGROUND OF THE INVENTION

1. Field of the Invention

This invention refers to a photonic sensing method and device for the detection of very small sized substances. More particularly, the invention is based on the physical properties of periodic dielectric structures of photonic forbidden band, over which the substances object of the sensing are placed.

2. Description of the Related Art

Nowadays, it is essential to have methods or devices for sensing that allow fast, efficient and reliable measurement of a large number of parameters, such as, temperature, pressure, electric field intensity, etc. In addition to the measurement of the aforementioned physical magnitudes (for which there already exist rather mature measurement methods), the main interest currently centers on the development of sensing devices or methods for the detection, identification and quantification of substances (which we shall call analyte) such as gas, liquids, proteins, hormones, bacteria, or DNA, amongst many others. These sensing devices and methods have applications in many fields, such as, pharmaceutical research, disease diagnosis, pollutant detection or the bacteriologic war.

The methods typically used for analyte detection are based on the use of so called markers. Through an adequate treatment of the sample containing the analyte to be detected (generally this method is carried out in a laboratory), a link of the marker used to the analyte is achieved. This marker consists of a material featuring specific physical properties, such as, fluorescence, radioactivity, etc., so that detection of the analyte is carried out indirectly, measuring the fluorescence, radioactivity, etc. in the sample containing the analyte. However, the use of markers to carry out sensing presents various problems, such as could be the need to do previous preparation of the sample to be analyzed (which may be complex and require a large amount of time) or the difficulty to find a method which sets the markers solely and specifically to the analytes we wish to detect.

It is, therefore, of great importance to have sensing devices or methods that enable the detection without the need to use markers. One of the options that currently raise the most interest is the use of photonic devices to carry out sensing functions. A photonic device is defined as one in which the frequency of spread signals is within the optical range of the spectrum. This type of devices have a certain material distribution with a certain refraction index n, so that the device's response is given by the refraction index of the materials comprising it, as well as by the shape that these materials feature in the structure. An example of a very common photonic device nowadays is fiber optic, which is a means of transmission in which there is a circular nucleus made of a material with a refraction index n1 surrounded by a coating of a material with a refraction index n2. Since the refraction index of the nucleus is higher than that of the coating (n1>n2), the light will remain confined to the nucleus due to the total internal reflection phenomenon and it will be able to propagate through the fiber. The fiber's frequency response will depend on various factors, such as the contrast of indices between the nucleus and the coating, the diameter of the nucleus, the coating's thickness, fiber's imperfections, etc.

In the case of fiber optic, the contrast between the nucleus and the coating indices is very small (under 1%), which causes the structure's nucleus to have a diameter of a few dozen microns. When the contrast of indices between the guide's nucleus and the material forming the coating increases, the confinement of the field in the high index region forming the guide's nucleus increases, therefore being able to significantly reduce the size of the devices. This is what is known as nanophotonics, where the use of materials with a high refraction index allows attainment of devices with a size in the hundreds of nanometers.

The field of nanophotonics has experienced significant evolution in the last few years, during which several structures have been developed for the implementation of functionalities in the optical domain, such as guiding, WDM filters, channel addition/extraction filters, commuters, etc. A great part of this evolution has been due to the possibility of using planar substrate structures, through which photonic circuits are created in flat layers of a certain material, with a certain thickness (e.g. Silicon, Silicon oxide, Silicon nitride, etc.), thus leading to integrated photonics. Precisely, when the materials used to create the integrated photonic circuits are compatible with those used in the microelectronics industry (e.g. Silicon, Silicon nitride, etc.), it is possible to make direct use of the manufacturing processes coming from that industry, thus enabling attainment of products with a reduced cost and apt for mass manufacturing.

The use of photonic devices to carry out sensing functions has been demonstrated by several research groups. The transduction technique used to carry out the sensing of those types of structures is the variation of the refraction index. As previously described, the response of a certain photonic device depends both on its shape or dimensions as well as the refraction index of the materials forming the device. This way, when the analyte to be detected causes a change in the refraction index of the structure over which it is placed (generally in the region above the guided element of the signal), this change may be detected through variation of the photonic device's response.

There are various configurations for photonic devices to carry out sensing functions. Currently, the most popular are based on resonance structures, such as disks or rings, which are coupled to an access guide (K. De Vos, I. Bartolozzi, E. Schacht, P. Bienstman, and R. Baets, "Silicon-on-Insulator microring resonator for sensitive and label-free biosensing," Opt. Express 15, 7610-7615 (2007) and C. A. Barrios, K. B. Gylfason, B. Sanchez, A. Griol, H. Sohlström, M. Holgado, and R. Casquel, "Slot-waveguide biochemical sensor," Opt. Lett. 32, 3080-3082 (2007)). This type of structures behaves as a cavity, so that only those modes whose wavelength fulfils the condition of resonance may exist in its interior. These wavelengths are extracted from the access guide, thus observing peaks rejected in its transmission spectrum. The position of the resonances depends on the refraction index of the material forming the structure. When making the detection, the substance to be detected is placed over the resonance structure, so that the variation in the refraction index of the material surrounding the structure causes certain displacement of the resonance position. This variation in wavelength of the resonance is used to determine the refraction index of the material placed over the structure. If carrying out sensing of a specific analyte (as opposed to detection of a homogeneous substance with a certain refraction index), the displacement of resonances indicates the quantity of analyte present in the fluid. Using this type of sensors, very high sensibilities have been demonstrated, attaining values over 200 nm/UIR (Refraction Index Unit) (K. De Vos, I. Bartolozzi, E. Schacht, P. Bienstman, and R. Baets, "Silicon-on-Insulator microring resonator for sensitive and label-free biosensing," Opt. Express 15, 7610-7615 (2007) and low detection limits of around 2×10-5 UIR (C.-Y. Chao, W. Fung, and L. J. Guo, "Polymer Microring Resonators for Biochemical Sensing Applications," IEEE J. Sel. Top. Quantum Electron. 12, 134-142 (2006).

Another type of photonic structures of great interest for the development of sensing devices are the periodic dielectric structures (occasionally also known as photonic crystals). This type of periodic structures, if an adequate design of the structure is executed (i.e. periodicity, size of elements forming the periodic structure, etc.) and the contrast of the refraction indices of material used to create the structure is sufficient, the so called forbidden photonic bands may appear (usually this region is known by its English term photonic band gap): frequency regions of the transmission spectrum in which propagation of the wave is not permitted (J. D. Joannopoulos, R. D. Meade, and J. N. Winn, Photonic Crystals: Molding the Flow of Light (Princeton U. Press, Princeton, N.J., 1995)). As with the case of resonant structures, the position of the forbidden photonic band also varies when the refraction index of the material comprising the structure is modified. This way, when placing a certain substance over the periodic structure, the displacement experienced by the forbidden photonic band may be used to determine the substance's refraction index (or the quantity of certain analyte present in the fluid). Instead of directly using the complete periodic structure, lineal or punctual defects may be introduced in order to create guides or cavities. In this case, what is used to carry out detection is the position of the guided mode (in the case of the guide) or the resonant mode (in the case of the cavity), in a way similar to the one described for the case of the complete periodic structure. The benefits achieved using this type of structures are not as high as those achieved using resonant structures, although a higher evolution of this technology is expected, allowing attainment of better results. The values currently demonstrated are sensibilities of around 65 nm/UIR and detection limits of around $1 \times 10$-4 UIR (N. Skivesen, A. Têtu, M. Kristensen, J. Kjems, L. H. Frandsen, and P. I. Borel, "Photonic-crystal waveguide biosensor," Opt. Express 15, 3169-3176 (2007)).

Both types of devices described above (resonant structures and dielectric periodic structures) base detection on the variation produced on the spectrum, either by wavelength displacement of the resonances, the photonic forbidden band, or the guided modes. There are, additionally, other integrated photonic structures allowing the execution of sensing functions directly using a signal's output amplitude of a certain wavelength, so that it is not necessary to carry out a scan providing the device's transmission spectrum. Examples of this type of sensing systems, based on amplitude, include the Mach-Zehnder interferometers (Th. Schubert, N. Haase, H. Ktick, and R. Gottfried-Gottfried, "Refractive-index measurements using an integrated Mach-Zehnder interferometer," Sens. Actuators A Phys. 60, 108-112 (1997)) or the directional couplers (B. J. Luff, R. D. Harris, J. S. Wilkinson, R. Wilson and D. J. Schiffrin, "Integrated-optical directional coupler biosensor," Opt. Lett. 21, 618-620 (1996)). Even though these systems are able to prevent the need to execute a frequency scan, providing simpler sensing devices, they have the problem that they require very large device dimensions (of a few millimeters) in order to have a sufficiently large interaction between the field and the analyte for detection, since they are only comprised of a dielectric guide through which the signal spreads, without producing an effect that allows an increase of the signal's interaction with the analyte. Therefore, due to this size, it is not possible to attain final devices with a high level of integration.

The photonic sensing method and device executed according to this invention is framed within the photonic sensors based on the direct measurement of the output amplitude, like those devices reported on (Th. Schubert, N. Haase, H. Ktick, and R. Gottfried-Gottfried, "Refractive-index measurements using an integrated Mach-Zehnder interferometer," Sens. Actuators A Phys. 60, 108-112 (1997) and B. J. Luff, R. D. Harris, J. S. Wilkinson, R. Wilson and D. J. Schiffrin, "Integrated-optical directional coupler biosensor," Opt. Lett. 21, 618-620 (1996)). However, unlike the technical solutions in those references, this invention features numerous advantages when implementing sensing systems, most of them derived from the small size of the dielectric structures utilized, which allows for an efficient interaction between those structures and the analytes to be sensed.

In addition to enabling a better interaction between the sensor and the analyte, the fact of having a reduced size facilitates, additionally, attainment of a high level of integration of the final device, which allows the use of a large number of sensitive photonic structures in a very small area, thus being able to carry out multiple simultaneous detections (e.g. for multi-analyte measurements, comparative analysis, etc.).

The possibility of using small-sized periodic structures makes it possible, additionally, for only very small substance volumes to be necessary (in the range comprised between milliliters and microliters, in the case of liquids, or micrograms and femtograms in the case of solids) to carry out detection of the analyte. An example of an embodiment of great interest would be that in which a detection of one (or several) substances is carried out in the blood using only a single drop of the fluid.

Another advantage of this invention with respect to the devices reported on [6] and [7], is that there is no need to use the guiding structures featured by those devices, either through index contrast guides or introducing lineal defects in the periodic structure. This need of guidance makes it, in practice, tremendously difficult to apply those techniques to tri-dimensional periodic structures, such as opals. Furthermore, large scale production of this type of devices would effectively be hardly attainable, since they do not allow for the use of manufacturing techniques from microelectronics. This invention, however, describes a photonic sensor that does not require the use of any guiding technique which naturally allows its application to tri-dimensional structures.

The design of the present invention, therefore, facilitates for the analytes to be sized under one nanometer, through a direct measurement of the sensor's output amplitude, thus preventing the need to obtain the spectral response from the device, which facilitates a simpler, more-direct sensing mechanism, applicable to all types of periodic dielectric structures.

SUMMARY OF THE INVENTION

An object of the present invention is to obtain photonic sensors with a simple design, using the variation in the refraction index of the material coating the dielectric structure as the transduction technique, through direct measurement of the output amplitude from a variation of the photonic forbidden band's position.

Another object of this invention is to obtain photonic sensors featuring a high level of integration, whose design is executed through small-sized structures, facilitating an efficient interaction between those structures and the analytes object of the sensing.

Another object of the present invention is to obtain photonic sensors that are adaptable to dielectric structures of one, two or three dimensions.

Another object of the present invention is a photonic sensing method for detection of substances or analytes with a very small size, where those analytes are arranged on a dielectric structure, periodic in the propagation direction of the waves that are transmitted through the structure, and which features a photonic forbidden band for transmission, in which:

a) There is the generation of, at least, one broad band signal through the periodic dielectric structure without and analyte, centered on the limit region of the photonic forbidden band, so that a power refraction of the excitation source remains within the photonic forbidden band, with that broad band signal being kept throughout the sensing process.

b) There is a direct measurement, without the need to obtain the response in frequency of the periodic dielectric structure, of the output power that has not been filtered by the photonic forbidden band.

c) The analyte object of study is arranged on the periodic dielectric structure.

d) There is direct measurement, without obtaining the response in frequency, of the variation in the quantity of power that has not been filtered by the photonic forbidden band.

e) Any properties of the analyte object of the sensing are determined, such as its refraction index and/or the amount of the analyte that has been deposited, from the variation in output quantity that has not been filtered by the photonic forbidden band, with respect to the value obtained before placement of the analyte on the periodic dielectric structure.

Another object of the present invention is a photonic sensing method in which the periodic dielectric structure used is a periodic dielectric structure of a planar substrate.

Another object of the present invention is a photonic sensing method in which the periodic dielectric structure used is a tri-dimensional periodic dielectric structure.

Another object of the present invention is a photonic sensing method in which the variation of the refraction index in the periodic dielectric structure is not produced as a consequence of depositing the analyte, but it varies through any other property, through which the refraction index of any of the parts forming that dielectric structure is modified, such as using materials that allow the absorption of certain analytes for the creation of the periodic dielectric structure, thus modifying its properties in terms of the refraction index.

Another object of the present invention is a photonic sensing method in which, through execution of a scaling of the network constant of the periodic dielectric structure, a sensing process is achieved regardless the range of frequencies of the broad band signal used.

Another object of the present invention is a photonic sensing method in which the excitation source and/or the signal detector are coupled, but optionally not integrated with the sensing structure.

Another object of the present invention is a photonic sensing method in which many periodic dielectric structures of a photonic forbidden band are used, or whichever other structures with an equivalent response, for the execution of multiple detections, regardless of each structure having its own excitation source or several structures being excited by the same source, with each periodic dielectric structure being usable to detect different analytes.

Another object of the present invention is a photonic sensing method in which instead of a periodic dielectric structure, another photonic structure providing an equivalent response is used, in which there is a certain range of frequencies which is not transmitted, or which undergoes a higher attenuation of its output power signal. An example of an alternative structure, with which the proposed method in this invention could be used, would consist on a rejected band filter created through the use of resonant rings, so that they provide a certain range of frequencies that are not transmitted (equivalent to a photonic forbidden band).

Another object of the present invention is a photonic sensing device for the detection of substances or analytes with a very small size, where those analytes are arranged on a dielectric structure, periodic in the direction of wave propagation which are transmitted through that structure, which comprises:

a) A periodic dielectric structure featuring a forbidden band of transmission.

b) At least one source of excitation connected to the periodic dielectric structure, designed to provide at least one broad band signal centered on the region of the edge of the photonic forbidden band, so that a fraction of power from the excitation source remains inside the photonic forbidden band.

c) At least one broad band power detector connected to the periodic dielectric structure, designed to indicate the quantity of output power that has not been filtered by the photonic forbidden band, so that the sensing may be executed directly, from the power variation produced when placing the analyte object of the study, without the need to obtain the response in frequency from the periodic dielectric structure.

Another object of the present invention is a photonic sensing device in which the periodic dielectric structure which forms the device is a planar substrate periodic dielectric structure.

Another object of the present invention is a photonic sensing device in which the periodic dielectric structure which forms the device is a tri-dimensional periodic dielectric structure.

Another object of the present invention is a photonic sensing device in which the refraction index variation of the periodic dielectric structure is not produced as a consequence of placing the analyte, but it varies through any other method, through which there is a modification of the refraction index of any of the parts forming the dielectric structure, such as using materials that allow the absorption of certain analytes for the creation of a periodic dielectric structure, thus modifying its properties in terms of refraction index.

Another object of the present invention is a photonic sensing device in which, through the execution of a scaling of the network constant of the periodic dielectric structure, a sensing process is obtained regardless of the frequency range of the broad band signal used.

Another object of the present invention is a photonic sensing device in which the excitation source and/or signal detector are coupled, but optionally not integrated with the sensing structure.

Another object of the present invention is a photonic sensing device in which multiple periodic dielectric structures of photonic forbidden bands are used, or whichever other structures with an equivalent response, for the execution of multiple detections, regardless of each structure having its own excitation source or several structures being excited by the same source, with each periodic dielectric structure being usable to detect different analytes.

Another object of the present invention is a photonic sensing device in which, instead of a periodic dielectric structure, another photonic structure providing an equivalent response is used, in which there is a certain range of frequencies which is not transmitted, or which undergoes a higher attenuation of its output power signal, for example using a rejected band filter created through the use of resonant rings, so that they provide a certain range of frequencies that are not transmitted, in a way equivalent to a photonic forbidden band.

Other characteristics of the present invention will emerge in the detailed description that follows, together with a preferred embodiment of its object.

For the purpose of the present invention, the following terms are defined:

Analyte: Any type of sample object of sensing, featuring a solid, liquid or gaseous state.

Substrate: A material over which the working photonic structure is created.

Planar substrate: A substrate that is formed through flat layers.

Network constant of the dielectric structure: A value that determines the distance between the repetitions of the basic cell, thus resulting in a periodic structure, i.e., the period of the structure in each of the periodicity dimensions.

Scaling: Transformation executed over the periodic dielectric structure, consisting of increasing or decreasing its network constant and the dimensions of all the elements forming the structure proportionally, so that there is a resulting expanded or reduced equivalent structure. This transformation causes a modification of the structure's working frequency range.

DETAILED DESCRIPTION OF THE PREFERRED EMBODIMENTS

This invention describes a photonic sensing method and device for the detection of very small sized substances or analytes, based on periodic dielectric structures of photonic forbidden band, over which the analytes are placed. The detection process executed by the invention's photonic sensor is carried out through measurement of the broad band signal's amplitude, exiting the dielectric structure, in the stages that comprise the before and after placement of the analyte object of study. The difference shown by the amplitude measurement at those stages is given by a variation of the refraction index of the periodic dielectric structure, as a consequence of the presence the analytes object of the sensing in the structure. This way, through an analysis of the photonic sensor's variation response, which depends both on the shape of the dielectric structure conforming the sensor as well as on the refraction index of the materials comprising it, the desired sensing behavior is attained.

The development of a photonic sensor according to the method and device described in this invention is based on the physical properties of the periodic dielectric structures (occasionally also known as photonic crystals), which may feature frequency regions in which wave propagation is not permitted, frequencies region that is known as photonic forbidden band (usually this region is known by its English term photonic band gap). The position of this photonic forbidden band depends on the refraction index of the material comprising the dielectric structure used, therefore, obtaining the photonic forbidden band's position, any variation of the dielectric structure's refraction index may be detected. In the general case of the method employed by the majority of photonic sensors (which is also applicable for this invention), the photonic forbidden band's position is obtained either using a source of signal that may be tuned in frequency and a broad band detector, or using a broad band source and a detector that may be tuned in frequency. From direct observation of the spectrum, the position of the photonic forbidden band is determined, which will enable determination of the substance's frequency index or the presence (and quantity) of a certain analyte.

Figure 1A:
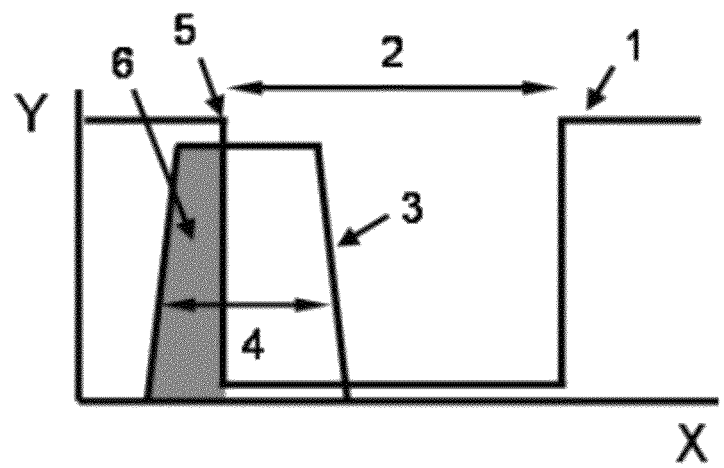
FIG. 1a represents the initial state of the signal's transmission spectrum (Y), through a periodic dielectric structure featuring a photonic forbidden band, as a function of the wavelength (X).
Figure 1B:
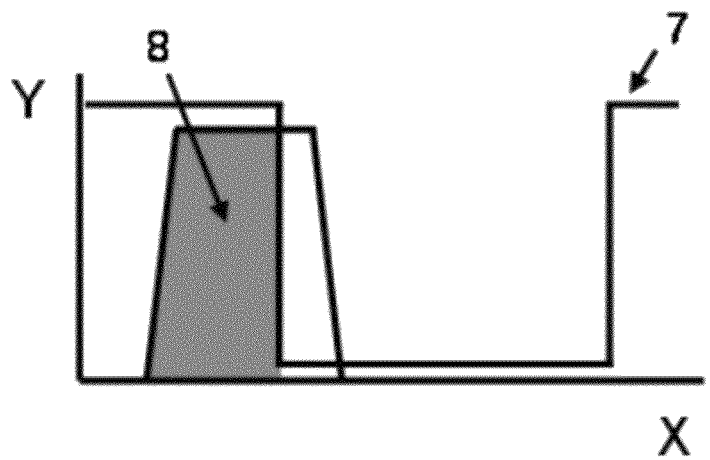
FIG. 1b represents the state of the signal's transmission spectrum (Y), through a periodic dielectric structure featuring a photonic forbidden band, after placing the substance object of the sensing, as a function of the wavelength (X).
Figure 1C:
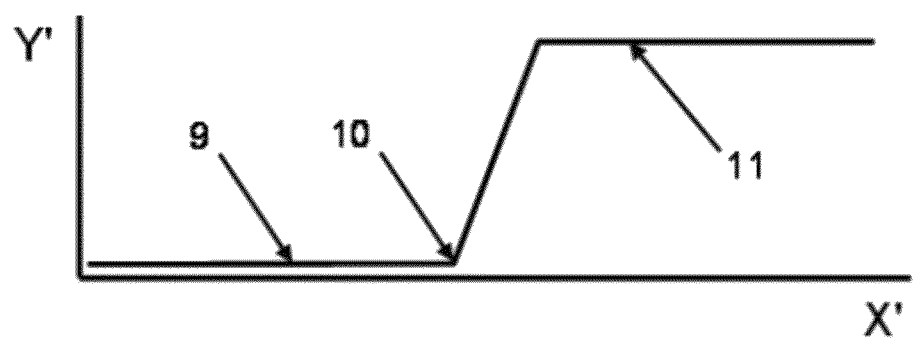
FIG. 1c shows the evolution in output power (Y') as a function of time (X'), for a device according to the present invention, in the stages before and after depositing the substance object of the sensing.

Additionally, in the present invention a method and a device, in which only the periodic dielectric structure's output power is used to carry out the detection, are proposed, so that it is not necessary to execute a frequency spectrum scan. The proposed method is described in FIGS. 1a, 1b and 1c. In FIG. 1a, the initial state is represented, in which there is the transmission spectrum (Y) of a periodic dielectric structure (1), featuring a photonic forbidden band (2) coating a certain range of wavelengths (X). In order to carry out the measurement, a signal source (3) is used, with certain band broadness (4), which is located on the extreme area of the photonic forbidden band (5). This way, the photonic forbidden band acts as a filter, only letting through part of the signal used as excitation (6). When measuring the output power using a broad band power meter, certain power value (9) is obtained, as shown on FIG. 1c, which is determined by the portion of the input power spectrum that has been filtered by the photonic forbidden band. In FIG. 1b, the state in which the substance or analyte wishing to be sensed was placed is shown. The substance or analyte causes a variation in the refraction index of the photonic structure, causing at the same time a displacement of the transmission spectrum (Y) of the periodic dielectric structure (7). FIG. 1b shows the case in which a substance with a higher refraction index than that of the one in the case represented in FIG. 1a, so that a displacement of the transmission spectrum (Y) occurs, towards higher wavelengths (X). As the transmission spectrum (Y) is displaced, there is, at the same time, a displacement of the photonic forbidden band. This causes a variation in the signal quantity from the excitation source that has been filtered (8). FIG. 1c shows the evolution of output power (Y') with time (X'), where it may be observed how, in the moment (10) in which the variation in the periodic dielectric structure's refraction index occurs, the displacement of the photonic forbidden band causes an increase in the structure's output power (Y') until the level of power (11) determined by the refraction index of the substance or analyte that was placed is reached.

Using the method described in the present invention avoids the use of sources or detectors that may be tuned in frequency to obtain the transmission spectrum of the photonic device to do the sensing. This way, measurement is simplified. The use of elements with a higher cost is avoided (such as sources and detectors that may be tuned) and real-time sensing is achieved.

In addition to the above characteristics, and due to the scaling properties featured on the periodic structures, the response of this invention's device may be implemented in any range of working frequencies, through execution of the appropriate scaling of the periodic structure's network constant, being able to obtain an equivalent sensing behavior, regardless of the frequency range used (i.e. infrared, microwave, terahertz, etc.).

Figure 2:
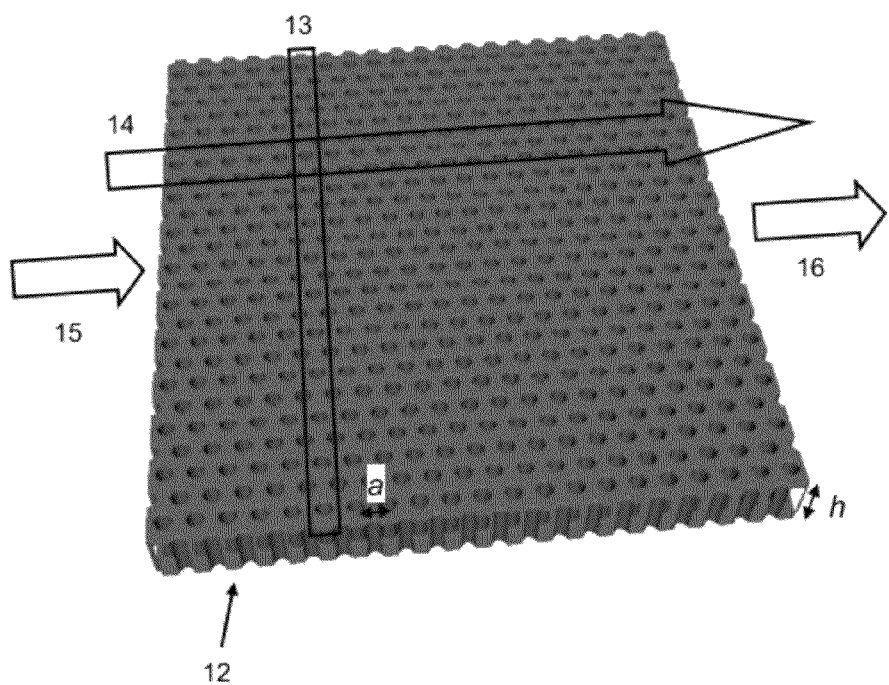
FIGS. 2, 3 and 4 show different configurations of the periodic dielectric structures that may be used to the implementation of a photonic sensor using the method described by the invention.
Figure 3:
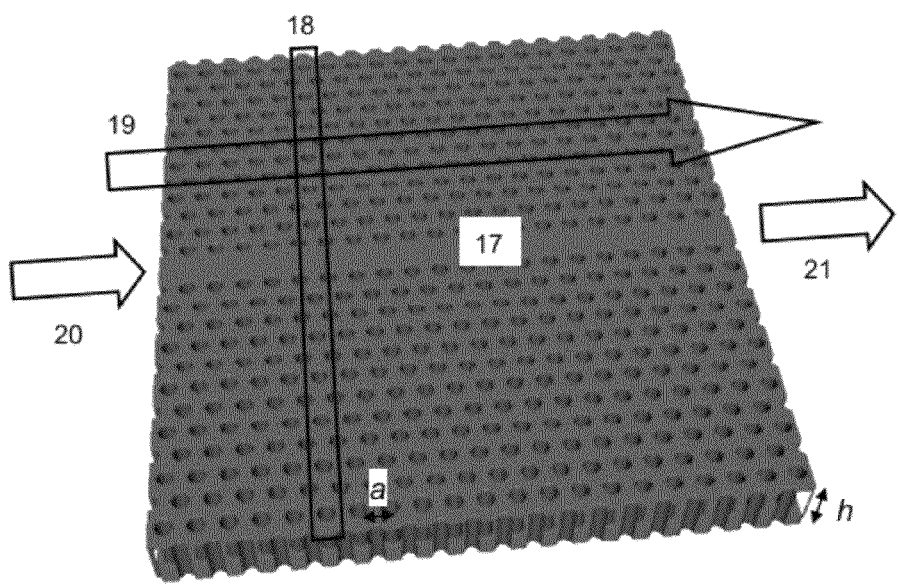
Figure 4:
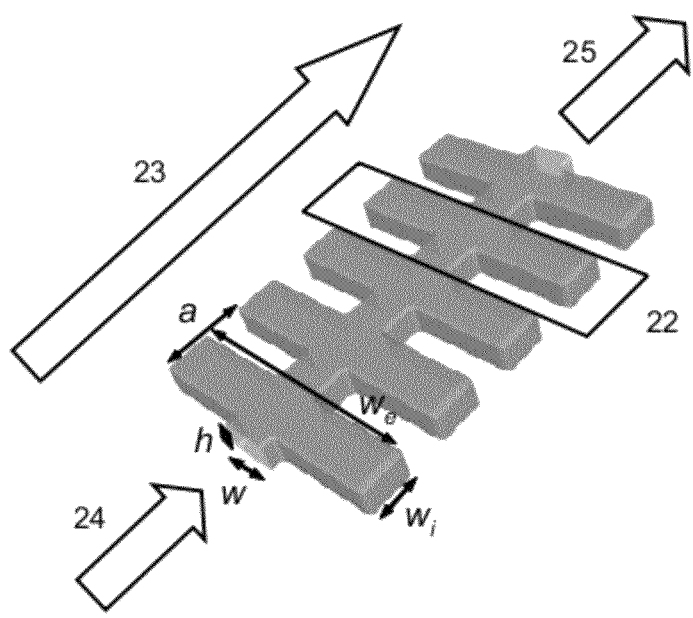

In order to achieve the photonic forbidden band necessary to carry out the sensing, any dielectric structure that is periodic in the direction of propagation may be used, since this characteristic is the one responsible for the occurrence of the photonic forbidden band. In FIGS. 2, 3 and 4 different configurations of periodic dielectric structures are shown, which may be used for the implementation of a photonic sensor, using the method described in this invention. FIG. 2 shows a planar dielectric structure (with an h height) which is periodic in two dimensions. The structure is formed by periodic network of holes created on a material with a high refraction index (12). Although the structure is periodic in two dimensions, for the execution of sensing functions, the periodicity of interest will be the one that is produced on the direction of wave propagation. The basic cell (13), which is the one that is periodically repeated in the direction of propagation (14), with an a period, has been represented. This way, if the structure has been adequately designed, it will feature a photonic forbidden band in the direction of propagation, according to what was previously described. In FIG. 2, the input signal to the structure (15) and the output signal (16) are also indicated.

In FIG. 3, another configuration of a planar dielectric structure (of h height) periodic in the propagation direction is shown. The structure is identical to the one shown in FIG. 2, but in this case, a lineal defect has been introduced to create a wave guide (17). The defect created in this case consists of eliminating a row of holes from the periodic structure (although multiple options for the introduction of defects in order to create wave guides will exist). Once again, we will have a basic cell (18) which repeats itself along the direction of propagation (19), with an a period. In this case, if the structure's design is correctly executed, both a photonic forbidden band and guided mode will be available. Any of them may be used to carry out the sensing, using the method described in this invention. Again, in FIG. 3, the input signal to the structure (20) and the output signal (21) are indicated.

FIG. 4 shows another possible configuration of the planar dielectric structure (of and h height) periodic in the direction of propagation. In this case, there is only one structure which is periodic in the direction of propagation, as opposed to the structures shown in FIGS. 2 and 3, in which there is an additional periodicity on the plane (bi-dimensional periodicity). The structure consists of a basic cell (22) formed by a rectangular transversal element with a wi width; and a we length introduced in a width guide w; this basic cell repeats itself along the direction of propagation (23) with a period a to achieve the complete periodic structure. There will be combinations of the structure parameters (i.e., period, width and length of the transversal elements, height and refraction indexes of the materials used) for which a photonic forbidden band may be present. In FIG. 4, the input (24) and output (25) signals of the structure are also indicated.

From the configurations displayed in FIGS. 2, 3 and 4, it may be concluded that the proposed method may be used with any dielectric structure that is periodic in the direction of propagation (regardless of it also being periodic in other dimensions), which features a photonic forbidden band.

This invention describes, thus, a photonic sensing method and device, using photonic sensing amplitude without the need to execute a frequency scan when working with periodic dielectric structures, regardless of the periodic structure used, the type of source and detector used to carry out the measurement, or the method used to create the sensing structure. In different preferred embodiments of the present invention, it is possible to use any structure, periodic in the direction of signal propagation, whether it be one, two or three dimensions, either through a planar substrate over which the periodic structures are formed in one or two dimensions, or through other types of structures, such as tri-dimensional photonic crystals or opals, as long as they feature the characteristic properties associated with the presence of a photonic forbidden band.

Figure 5:
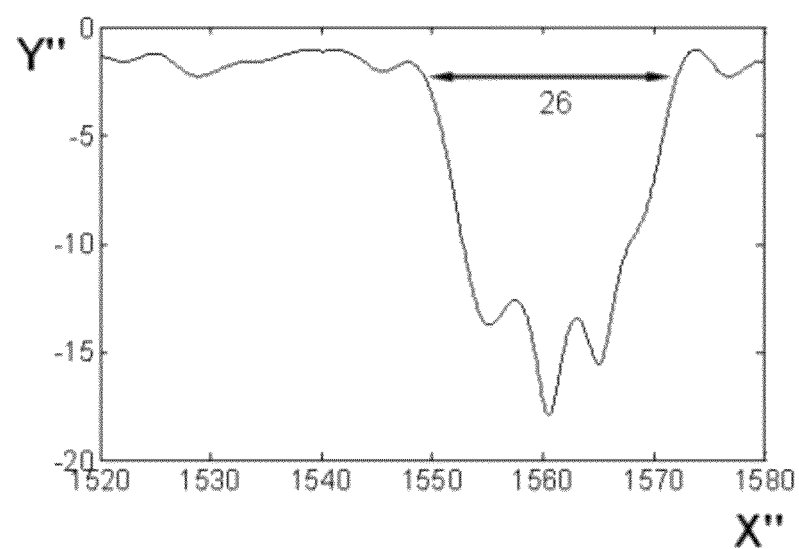
FIG. 5 shows a photonic forbidden band obtained in the only preferred embodiment of the present invention that is provided in the description, where the normalized transmission (Y"), expressed in dB is represented, versus the wavelength (X"), expressed in nanometers.

In order to illustrate the sensing method and device proposed in this invention, we choose the preferred embodiment that is represented in FIG. 4. The periodic structure is created with Silicon, and is surrounded by air. From a single mode guide, with a h=250 nm height and a w=500 nm width. In this guide, the transversal elements are introduced, in a periodic fashion, to form the basic cell. The transversal elements have dimensions of $w_i$=110 nm and $w_e$=2 µm. Selecting a period of a=300 nm, a photonic forbidden band is achieved from the normalized transmission (Y") for the modes with a TE polarization (the polarization is defined as one for which the electric field has its components on the plane of the planar structure) approximately between wavelengths (X") of 1550 nm and 1570 nm, as shown on FIG. 5 (26).

When the signal coming from a source of excitation is introduced to the periodic dielectric structure, with a band broadness of 5 nm and centered on the wavelength of 1556 nm, a certain power level P1 is obtained at the output, which is determined by the power of the input signal used and the device's losses (i.e. coupling losses, propagation losses, etc.). At the moment in which a substance is placed over the periodic dielectric structure with a refraction index of n>1 (based on the case in which there is air over the periodic dielectric structure whose n=1), there is a variation in the response of the periodic dielectric structure, which causes a displacement of the photonic forbidden band towards higher wavelengths (since an increase of the refraction index of the material covering the structure has taken place). This displacement of the photonic forbidden band causes a variation in the optical power measured at the device's exit, becoming a P2 measurement, which will be higher than P1. This power level P2 allows determination of either the refraction index of the deposited substance, or the presence and quantity of certain analyte to be detected. Precisely, for a preferred embodiment, a structure sensibility to the variations in refraction index of approximately 20 nm/UIR has been estimated. This sensibility is the one that determines the photonic forbidden band's displacement, when the refraction index of the material surrounding the structure varies. With the sensing method proposed herein, it has been experimentally proven how this sensibility, in terms of refraction index, translates to a sensibility in terms of power of approximately 50 dB/UIR. It is worth noting that this sensitivity value is only valid for the refraction indices margin that cause the photonic forbidden band to be present within the wavelength range of the excitation source used. Considering a resolution in the power measurement of about 0.001 dB (which may be achieved with current power meters; significantly higher resolution values could also be achieved carrying out temporary averaging), a detection limit of 2×10-5 could be achieved (which, as has been previously discussed, could be even less) In case a certain analyte is being measured, the sensitivity values and detection limits are characterized by the own analyte's intrinsic properties: size, mass, refraction index in the range of working wavelengths, etc.

The invention claimed is:

1. A photonic sensing method for detection of analytes, said analytes being placed on a dielectric structure, periodic in a propagation direction of waves that are transmitted through said structure, and which features a photonic forbidden band for transmission, the method comprising:
   a) generating at least one broad band signal from an excitation source and through the periodic dielectric structure without an analyte, the signal being centered on an edge region of the photonic forbidden band, so that a fraction of a power of the excitation source remains within the photonic forbidden band, said broad band signal being maintained throughout the sensing method;
   b) directly measuring, without obtaining a frequency response from the periodic dielectric structure, an output power quantity that has not been filtered by the photonic forbidden band;
   c) placing the analyte on the periodic dielectric structure;
   d) directly measuring, without obtaining a frequency response, the output power quantity that has not been filtered by the photonic forbidden band;
   e) determining one or more properties of the analyte based on the variation in the output quantity that has not been filtered by the photonic forbidden band, with respect to the output quantity obtained before placing the analyte on the periodic dielectric structure.

2. The photonic sensing method of claim 1, wherein the periodic dielectric structure is a planar substrate periodic dielectric structure.

3. The photonic sensing method of claim 1, wherein the periodic dielectric structure is a tri-dimensional periodic dielectric structure.

4. The photonic sensing method of claim 1, wherein the variation of the refraction index of the dielectric periodic structure is not produced as a result of placing the analyte, but rather varies through any other property, through which there is a modification of the refraction index of any of the parts forming the dielectric structure, thereby modifying the properties in terms of the refraction index.

5. The photonic sensing method of claim 1, further comprising scaling of a network constant of the periodic dielectric structure, so that a sensing process is obtained regardless of the frequency range of the broad band signal used.

6. The photonic sensing method of claim 1, wherein at least one of the excitation source and signal detector are integrated in the sensing structure or are external to the structure.

7. The photonic sensing method of claim 1, further comprising using multiple periodic dielectric structures of photonic forbidden band for executing multiple detections, regardless of whether each structure has its own excitation source or that several structures are excited by the same source, with each periodic dielectric structure being usable to detect different analytes.

8. A photonic sensing method for detection of analytes placed on a photonic structure that provides a response to a luminous excitation source in which there is a certain range of frequencies that are not transmitted, or undergo a higher attenuation in an output power signal to provide a certain range of frequencies that are not transmitted in a way equivalent to a photonic forbidden band, the method comprising:
   a) generating at least, one broad band signal from an excitation source and through the periodic dielectric structure without an analyte, the signal being centered on a limit region of the forbidden band, so that a power refraction of the excitation source remains within the photonic forbidden band, the broad band signal being kept throughout the sensing method;
   b) directly measuring without obtaining a frequency response from the periodic dielectric structure, the output power quantity that has not been filtered by the photonic forbidden band;
   c) placing the analyte on the periodic dielectric structure;
   d) directly measuring without obtaining a frequency response, the output power that has not been filtered by the photonic forbidden band; and
   e) determining one or more properties of the analyte based on a variation in the output quantity that has not been filtered by the photonic forbidden band, with respect to the output quantity obtained before placing the analyte on the periodic dielectric structure.

9. A photonic sensing method according to claim 8, wherein the photonic structure used comprises a rejected band filter created through the use of resonant rings.

10. A photonic sensing device for analyte detection, where said analytes are placed on a dielectric structure, periodic in a propagation direction of waves that are transmitted through said structure, which comprises:
    a) a periodic dielectric structure having a forbidden band of transmission;
    b) at least one excitation source connected to the periodic dielectric structure, designed to provide at least one broad band signal centered on a region of an edge of the photonic forbidden band, so that a fraction of the power from the excitation source remains inside the photonic forbidden band; and
    c) at least one broad band power detector connected to the periodic dielectric structure, designed to indicate the quantity of output power that has not been filtered by the photonic forbidden band, so that the sensing may be executed directly, from a power variation produced when placing the analyte without obtaining the response frequency from the periodic dielectric structure.

11. The photonic sensing device of claim 10, in which the periodic dielectric structure forming said device is a planar substrate periodic dielectric structure.

12. The photonic sensing device of claim 11, wherein the periodic dielectric structure forming said device is a tri-dimensional periodic dielectric structure.

13. The photonic sensing device of claim 10, wherein the variation of the refraction index of the dielectric periodic structure is not produced as a result of placing the analyte, but rather varies through any other property, through which there is a modification of the refraction index of any of the constituent parts forming the dielectric structure, using materials allowing absorption of certain analytes for creating a periodic dielectric structure, thus modifying its properties in terms of refraction index.

14. The photonic sensing device of claim 10, further comprising means for executing a scaling of a network constant of the periodic dielectric structure and for obtaining a sensing process regardless of a frequency range of the broadband used.

15. The photonic sensing device of claim 10, wherein at least one of the excitation source and signal detector are either integrated in the sensing structure or are external to the structure.

16. The photonic sensing device of claim 10, wherein multiple periodic dielectric structures of photonic forbidden band are used for executing multiple detections, regardless of whether each structure has its own excitation source or several structures are excited by one source, with each periodic dielectric structure being usable to detect different analytes.

17. A photonic sensing device for the detection of analytes, which comprises:
   a) a photonic structure that provides a response to a luminous excitation source in which there is a certain range of frequencies that are not transmitted, or undergoes a higher attenuation in its output power signal, to provide a certain range of frequencies that are not transmitted to define a photonic forbidden band;
   b) at least one source of excitation connected to the periodic dielectric structure, designed to provide at least one broad band signal centered on a region of an edge of the band of frequencies that are not transmitted, so that a fraction of power from the excitation source remains within the band of frequencies that are not transmitted; and
   c) at least one broad band power detector connected to the periodic dielectric structure, designed to indicate the quantity of output power that has not been filtered by the band of frequencies that are not transmitted, so that the sensing may be executed directly, from the power variation produced when placing the analyte without obtaining the response in frequency from the photonic structure.

18. The device of claim 17, where the photonic structure used comprises a rejected band filter created through the use of resonant rings.

* * * * *